United States Patent [19]

Raehse et al.

[11] Patent Number: 5,785,859
[45] Date of Patent: Jul. 28, 1998

[54] OPTIMIZED PROCESS FOR CONDITIONING STEAM-BASED VAPOR STREAMS

[75] Inventors: Wilfried Raehse, Duesseldorf; Reiner Vogler, Emmerich; Johann F. Fues, Grevenbroich; Wilhelm Beck, Duesseldorf; Kathleen Paatz, Duesseldorf; Truc Tran Anh, Duesseldorf; Levent Yueksel, Duesseldorf, all of Germany

[73] Assignee: Henkel Kommanditgesellschaft auf Aktien, Duesseldorf, Germany

[21] Appl. No.: 682,796

[22] PCT Filed: Jan. 23, 1995

[86] PCT No.: PCT/EP95/00228

§ 371 Date: Oct. 18, 1996

§ 102(e) Date: Oct. 18, 1996

[87] PCT Pub. No.: WO95/21010

PCT Pub. Date: Aug. 10, 1995

[30] Foreign Application Priority Data

Feb. 1, 1994 [DE] Germany ............... 44 02 883.0

[51] Int. Cl.$^6$ ............... B01D 47/00; B01D 61/00
[52] U.S. Cl. ............... 210/651; 210/650; 55/228; 55/233; 95/188; 95/211; 95/229
[58] Field of Search ............... 55/228, 233; 95/188, 95/211, 229; 210/650, 651, 774

[56] References Cited

U.S. PATENT DOCUMENTS

| | | | |
|---|---|---|---|
| 2,555,287 | 5/1951 | Hadden | 95/188 |
| 3,651,617 | 3/1972 | Hodgson | 95/188 |
| 3,927,153 | 12/1975 | Tarhan | 261/128 |
| 4,143,072 | 3/1979 | Hetzel et al. | 260/573 |
| 4,188,290 | 2/1980 | Graham | 95/188 |
| 4,265,642 | 5/1981 | Mir et al. | 55/85 |
| 4,642,904 | 2/1987 | Smith | 34/9 |
| 4,751,003 | 6/1988 | Raehse | 210/651 |
| 5,302,300 | 4/1994 | Porri | 95/188 |
| 5,431,780 | 7/1995 | Raehse et al. | 159/48.1 |
| 5,492,626 | 2/1996 | Uenoyama | 95/188 |
| 5,582,634 | 12/1996 | Burdis | 55/228 |

FOREIGN PATENT DOCUMENTS

| | | | |
|---|---|---|---|
| 8813209 | 9/1988 | Austria | 95/188 |
| 1076481 | 5/1977 | Canada | 95/188 |
| 1076520 | 5/1977 | Canada | 95/188 |
| 1076521 | 6/1977 | Canada | 95/188 |
| 1088978 | 7/1994 | Canada | 95/188 |

(List continued on next page.)

OTHER PUBLICATIONS

Die Praxis des organischen Chemikers, 33rd Edition (1948), Walter De Gruyter & Co. Verlag, pp. 26–28 and 252.

Ullmanns Encyklopädie der technischen Chemie, 4th Ed., vol. 11 (1976) pp. 479–486.

(List continued on next page.)

Primary Examiner—Ernest G. Therkorn
Attorney, Agent, or Firm—Ernest G. Szoke; Wayne C. Jaeschke; Real J. Grandmaison

[57] ABSTRACT

The invention relates to an optimized process for conditioning a stream of superheated steam laden with steam-volatile organic components by condensation of the steam phase with recovery of the heat of condensation and at least partial separation of the steam-volatile organic components from the water-based condensate. The process operates with a first heat exchange stage in which the continuously introduced vapor stream is combined with a circulated and cooled liquid stream of condensed vapors. In a following second energy transfer stage, heat is indirectly removed from the liquid stream thus heated. A sidestream is removed from the liquid circuit of the condensed vapors and subjected to separation in a membrane process while the rest of the liquid stream is returned to the first stage.

The invention also relates to the use of this working principle for industrial applications, more particularly for the separation of organic mixtures by superheated steam and/or the drying of water-based useful-material preparations with superheated steam as the drying gas.

12 Claims, 2 Drawing Sheets

FOREIGN PATENT DOCUMENTS

| | | | |
|---|---|---|---|
| 283 862 | 9/1988 | European Pat. Off. | 95/188 |
| 34 47 867 | 7/1986 | Germany | 95/188 |
| 40 30 688 | 4/1992 | Germany | 159/481 |
| 43 07 115 | 3/1993 | Germany | 95/188 |
| 42 04 035 | 8/1993 | Germany | 95/188 |
| 42 04 090 | 8/1993 | Germany | 95/188 |
| 42 060 50 | 9/1993 | Germany | 95/188 |
| 42 064 95 | 9/1993 | Germany | 95/188 |
| 42 065 21 | 9/1993 | Germany | 95/188 |
| 42 087 73 | 9/1993 | Germany | 95/188 |
| 42 094 32 | 9/1993 | Germany | 95/188 |
| 42 34 376 | 4/1994 | Germany | 95/188 |
| 42 37 934 | 5/1994 | Germany | 95/188 |
| 43 26 468 | 2/1995 | Germany | 95/188 |
| 997968 | 7/1965 | United Kingdom | 95/188 |
| WO 87/00765 | 2/1987 | WIPO | 34/9 |

OTHER PUBLICATIONS

Kirk–Othmer Encyclopedia of Chemical Technology, 3rd Ed., vol. 9 (1980) pp. 816–820.

Vegetable Oils and Fats Processing, vol. II (1983), Interstampa–Rome, chapter VII, pp. 221–251.

Taschenburch für Lebensmittelchemiker und –Technologen, vol. 2, Springer Verlag, Berlin 1991, pp. 101–103.

Membrane Processes for Separating Liquid Mixtures, VEB Deutscher Verlag für Grundstoffindustrie, Leipzig 1977, pp. 76–91.

Ultrafiltratin Handbook, Technomic Publishing Co., Inc., Lancaster, Basel, 1986, pp. 1–8.

OPTIMIZED PROCESS FOR CONDITIONING STEAM-BASED VAPOR STREAMS

BACKGROUND OF THE INVENTION

1. Field of the Invention

The teaching according to the present invention addresses the problem of improving the separation of steam-based vapor streams which accumulate in various industrial processes at least partly in admixture with components of organic origin. The problem in question may be briefly defined as follows:

In the conditioning of useful materials and mixtures of useful materials of at least partly organic origin on an industrial scale, steam-based vapor streams containing more or less highly steam-volatile organic components as mixture constituents accumulate in very large quantities in various fields of application. These organic mixture constituents may be useful materials and/or pollutants which have to be recovered from the steam either to obtain useful materials or to prevent the release of impurities into the environment, particularly via the wastewater. A particular difficulty in solving this problem is that the condensation of the vapor streams laden with the organic components to form the aqueous liquid phase often leads to the formation of such stable emulsions that simple and economically viable phase separation is not possible. Solutions known from the prior art include, for example, the use in a separate process step of liquid solvents, the use of demulsification aids, the use of flocculants and/or precipitants and the like. Steam-volatile components cannot of course be removed from the corresponding condensate of the laden steam phase if the steam-volatile organic components are so highly soluble in water, even in the cooled state, that they do not form a homogeneous solution with the vapors cooled to form the liquid phase.

Steam phases laden with organic useful materials and/or pollutants accumulate in various industrial processes. Without any claim to completeness, a few characteristic examples are mentioned at this juncture: the working principles of steam distillation for separating organic mixtures and, above all, for purifying corresponding useful materials or mixtures of useful materials are established chemical knowledge, cf. for example L. Gattermann "Die Praxis des organischen Chemikers", 33rd Edition (1948), Walter De Gruyter & Co. Verlag, pages 26 to 28 and 252. On an industrial scale, this principle is applied, for example, in the purification of fats and oils of vegetable or animal origin where treatment of the prepurified material with steam is usually one of the last process steps. The relevant literature includes, for example, "Ullmanns Encyklopäidie der technischen Chemie", 4th Edition, Vol. 11 (1976), pages 479 to 486; Kirk-Othmer "Encyclopedia of Chemical Technology", 3rd Edition, Vol. 9 (1980), pages 816 to 820 and E. Bernardini "Vegetable Oils and Fats Processing" in "Oilseeds, Oils and Fats", Vol. II (1983), Interstampa-Rome, Chapter VII, pages 221 to 251 (Deodorization of Fats and Oils). The more recent literature includes D. Osteroth "Taschenbuch für Lebensmittelchemiker und -Technologen", Vol. 2, Springer Verlag, Berlin 1991, 101 to 103. This literature reference describes in particular modern processes for deodorization and purification by steaming in the refining of fats and oils using the principle of stripping with steam in vacuo.

However, purification or rather deodorization is not only important for raw materials. Products of chemical syntheses and products of the chemical transformation of raw materials of natural origin also require such purification steps. Examples of relevant applications include the processing of fatty acids, the purification of fatty alcohols and the production of, in particular, liquid esters which can be processed to cosmetics, pharmaceuticals and foods.

Another typical, industrially significant field for the use of purification by steaming is the removal of residues based on ethylene oxide and/or propylene oxide from reaction products which have been prepared by ethoxylation and/or propoxylation of organic compounds containing at least one active hydrogen atom. Compounds of this type are important as nonionic surfactants or as intermediate products for the products of anionic surfactant compounds. They are used, for example, in wetting agents, detergents and cleaning compositions and, to a large extent, in cosmetics or pharmaceutical auxiliaries. From their production, the reaction products initially obtained contain traces of ethylene oxide and/or propylene oxide and unwanted secondary reaction products, such as dioxane. The removal of these residues from the alkoxylated derivatives is a legal requirement and an essential step of the production process. Steam distillation or rather treatment of the reaction products initially obtained with steam to remove the unwanted impurities is the relevant process step carried out on an industrial scale in practice, cf. for example EP-A1-0 283 862, DE-A1-34 47 867, U.S. Pat. No. 4,143,072 and the literature cited therein.

2. Discussion of Related Art

Vapor streams based on superheated steam containing steam-volatile useful materials and/or pollutants accumulate on a large scale in the drying of water-containing useful materials and mixtures thereof, especially in the drying of corresponding aqueous preparations using steam superheated under the process conditions as the drying gas. Drying processes of this type have recently acquired increasing significance. The material to be dried can be processed in moving beds and/or fluidized beds. Recently, superheated steam has even been proposed for use in the spray drying of aqueous preparations. Full particulars of the application of drying with superheated steam in the production of wetting agents, detergents and/or cleaning compositions can be found in the following documents which all go back to work done by applicants: DE-A 40 30 688, DE-A 42 04 035, DE-A 42 04 090, DE-A 42 06 050, DE-A 42 06 521, DE-A 42 06 495, DE-A 42 08 773, DE-A 42 09 432 and DE-A 42 34 376, more particularly in earlier German patent applications DE-A 42 37 934 and DE-A 43 07 115. The teaching of these documents makes use of the principle of drying aqueous preparations of useful materials and mixtures thereof with superheated steam. Correspondingly laden steam is removed from the drying zone and, after reheating, is recirculated to the drying zone. That part of the circulating stream which corresponds to the water evaporated is removed from the circuit and condensed. It is precisely in the field in question, i.e. organic components for wetting agents, detergents and cleaning compositions, that highly stable, very fine-particle emulsions accumulate during the condensation of the vapor stream removed from the circuit, presenting considerable problems in terms of technically appropriate and economically viable conditioning. On the other hand, the unpurified stream of the condensed emulsate cannot be discharged into the environment as wastewater.

Irrespective of the problems referred to thus far, a continuing problem lies in the economic development of corresponding drying and/or steaming processes. The economy of industrial processes demands the complete recycling of the evaporation energy of the vapor stream removed or rather the heat of condensation released during its condensation. If it is considered that, in an industrial spray drying tower, for example of the type used for drying useful materials in the production of detergents, evaporation levels of 4 to 6 tonnes of water per hour can be achieved, it will readily be appreciated that an economic use must be found for the levels of energy released by steam condensation.

However, the problem addressed by the present invention is also encountered in other related fields, for example in the recovery of steam-volatile components from starting materials associated with the following fields: foods (including luxury foods) and starting materials for their production, preparations containing flavorings (for odor and taste), preparations from the fields of cosmetic and pharmaceutical auxiliaries and/or useful materials and the like. The conditioning of starting materials such as these using superheated steam either to dry corresponding aqueous preparations or to recover steam-volatile useful materials or mixtures thereof is the subject of earlier German patent application DE 43 26 468.

The problem addressed by the present invention, which is described in detail hereinafter, is to resolve the two main problem areas in the conditioning and disposal of streams of steam at least partly containing organic useful materials in technically improved form in a combined process. These two main problem areas are the simplified separation of the vapor condensate into—on the one hand—at least substantially pure water and—on the other hand and separately—the steam-volatile component(s) and the possibility of optimized energy recovery from the condensation of the steam-based vapor stream which has been run off as product stream from the previous process step.

The solution to this problem as defined in the following lies in the combination of a condensation step controlled in a certain way with subsequent membrane separation for separating the condensed liquid phase.

DESCRIPTION OF THE INVENTION

In a first embodiment, therefore, the present invention relates to a process for the optimized conditioning of a stream of superheated steam laden with steam-volatile organic components (hereinafter also referred to as the "vapor stream"), which may also be present as steam superheated under the process conditions, by condensation of the steam phase with recovery of the heat of condensation and at least partial separation of the steam-volatile organic components from the water-containing condensate.

The process according to the invention is characterized in that the heat to be removed from the continuously introduced vapor stream for its condensation is transferred at least predominantly by direct contact to a circulated, cooled liquid stream of condensed vapors, the energy taken up is transferred from this circulated stream to a second carrier by indirect heat transfer, a sidestream is removed from the condensed vapor circuit and is subjected to separation by a membrane separation process.

The teaching according to the invention encompasses the application of this process principle to the condensation and demulsification of vapor streams from the drying of useful materials and/or mixtures of useful materials for the production of wetting agents, detergents and/or cleaning compositions with hot gases, superheated steam in particular having been used as the hot gas in a spray drying or fluidized bed drying process.

In another embodiment, the present invention relates to the use of the process described above for conditioning streams of superheated steam from the distillation-based separation of multicomponent mixtures of at least partly organic origin by steaming.

Further embodiments of the invention include the application of this process principle to the recovery of useful materials, more particularly flavorings and/or fragrances, during their production and/or purification from a useful material which is preferably liquid and/or solid under normal pressure and temperature conditions. Finally, the invention relates to the application of this process principle for the removal of pollutants from and for the disposal of correspondingly contaminated steam-based vapor streams.

Particulars of the Teaching According to the Invention

The process principle according to the invention can be applied in a plurality of special embodiments. A number of these embodiments are illustrated in the accompanying drawings which will be described in detail in the following. All the special embodiments are characterized by combinations of the following essential process elements:

The vapor stream laden with organic components which is to be conditioned is condensed by direct contact and heat exchange with a selected liquid stream, the heat generated in the process being taken up and dissipated. A specially cooled liquid stream of condensed and circulated vapors is used as the condensation and cooling medium and for taking up the condensation energy released. The circulating vapor stream now laden with the energy taken up—but kept in the liquid phase—is brought into indirect heat exchange with a second carrier. The energy taken up is transferred to the second carrier by indirect heat exchange. In addition, a sidestream is removed from the condensed vapor circuit and subjected to separation in a single-stage or multiple-stage membrane separation process. The separation of the liquid streams, their cooling and the rate at which they are circulated are adapted to the overall process conditions so that a quasi-steady state is established throughout the continuous process. As will be seen in the following, the particular embodiment for each individual case is very largely determined by the individual parameters to be taken into account as a whole. However, the understanding of the teaching according to the invention and the principles by which it is determined in conjunction with specialist knowledge enables each particular individual case to be adapted to the parameters to be taken into account.

In the following, the elements determining the process as a whole are discussed separately from one another, their combination and adaptation to the particular application in question then being obtained by application of general expert knowledge.

If the continuous process is to be carried out without interruption, it is crucially important to keep the circulating vapor condensate stream used as direct coolant at the right temperature. This is illustrated, for example, by the application of the process to the drying of useful materials used in the production of wetting agents, detergents and/or cleaning compositions with superheated steam. The vapor stream removed from this drying stage, which is the "vapor stream" to be treated under the definition of the conditioning process in question, will generally be laden with a plurality of steam-volatile components of the dried mixture of useful materials which are generally present as impurities therein. Thus, it is known that, for example, anionic surfactants based on fatty alcohol sulfates (FAS) contain residues of unreacted fatty alcohols which are discharged as steam-volatile components during drying with superheated steam. So far as the process according to the invention is concerned, they are thus steam-volatile organic components to be separated from the condensed aqueous phase. However, fatty alcohols of the type in question can have melting points of, for example, 50° C. or even higher. If the vapor stream present in the vapor phase were to be cooled in contact with the previously condensed and circulated vapor condensate to such an extent that its temperature fell below the solidification temperature of the particular organic constituents present (i.e. fatty alcohols, for example, in the present case), the outcome would be an aqueous condensate stream charged with very fine-particle solids which might even assume a plastic character. It will immediately be appreciated that the circulation of such a stream can give rise to considerable difficulties, for example during spraying of the solids-laden liquid phase in the spray nozzle; in particular, however, the sidestream branched off from this solids-laden circulating stream would present difficulties in the membrane separation process. Rapid coating of the membrane surface and hence blockage thereof would be the outcome.

According to the invention, therefore, the circulating stream of the vapor condensate used as direct coolant and, in particular, the sidestream thereof introduced to the membrane separation stage are kept at a temperature which rules out any danger of blockage of the liquid circuit and, in particular, the membrane surface by condensed organic components. In the specific case in question, this means the only limited cooling of the circulating vapor condensate stream by subsequent indirect heat transfer, as defined above, to a second carrier with removal of the energy taken up during the direct condensation. More specifically, it could be useful for example to set the lower temperature limit of the circulating vapor stream or at least the sidestream removed for membrane separation at around 60° or 70° C. in order in this way to preclude the formation of fine-particle and optionally plastic solid phases in these liquid streams.

This limitation is not an actual restriction so far as the practical application of the process according to the invention is concerned. In effect, it is not only the temperature of the cooling liquid introduced which is crucial to the continuous uptake of the condensation energy by direct heat exchange in the first stage with the entire liquid phase accumulating remaining intact, freedom of choice also exists in the quantity of cooling liquid introduced. If, therefore, the temperature of the circulated cooling liquid can only be reduced to a limited extent in the case in question, the necessary energy uptake capacity can nevertheless be made available in the first direct cooling stage—despite the accumulation of large quantities of vapor stream—by increasing the rate of circulation of the cooling liquid.

It is obvious that the situation illustrated here does not apply when the organic constituents introduced with the vapor stream are soluble in water or are present as liquid phases even at comparatively low temperatures. Similar circumstances prevail in many practical applications, for example in the recovery of flavorings or even in the separation of pollutants, such as lower alkylene oxides.

In important applications, the following considerations can be imported. The combined condensate stream accumulating by direct energy exchange with the circulated liquid stream generally contains a considerable proportion of organic compounds in the form of a very fine emulsion. These emulsions undergo at best minimal, if any, separation into separate phases in the time available in the continuous process. However, part of the organic components introduced in the vapor stream tend to undergo sufficiently rapid demulsification for a generally floating organic phase to be formed over an aqueous organic emulsion phase, for example in an intermediate holding tank. Now, according to the invention, demulsified parts of the steam-volatile organic components are preferably removed from the liquid vapor condensate by phase separation after the direct exchange of energy to the separated phase, only that part or at least substantially only that part of the liquid condensate phase which contains the aqueous organic, dissolved and/or stably emulsified organic components being delivered to the process circuit. Irrespective of this, it can be crucial—in particular to the quality of the liquid sidestream to be introduced into the membrane separation stage—only or at least predominantly to use corresponding liquid phases. All the process parameters in question are technologically simple to put into practice and do not affect the flow rate, even in the case of large quantities of condensate such as accumulate, for example, in the spray drying of water-containing starting materials, for example in the field of detergents.

An important aid for the problem-free application and adaptation of the conditioning process according to the invention lies in the possibility of carrying out the process as a whole or at least each of the individual process stages under normal pressure. So far as the cooling of the vapor stream to be conditioned in the first direct energy exchange is concerned, this means an upper limit to the temperature of the aqueous phase accumulating as a whole of around 100° C., maximum temperatures of the liquid circulating stream above 90° C., for example in the range from about 90° to 95° C., being preferred. The building up of large temperature gradients can be useful both for the first direct exchange of energy and for the following, indirect second transfer of energy to a separate carrier stream, although it is important in this regard to bear in mind the principles discussed in the foregoing which derive in particular from the quality and from the nature of the organic steam-volatile components of the vapor stream.

The direct condensation forming the first stage of the process, in which the heat of the vapor stream introduced is transferred to the circulated stream of the vapor condensate, may be carried out by methods known per se. In a particularly simple embodiment, this stage of the process is carried out by condensation of the vapor sidestream in a countercurrent washing unit through which the vapor phase and the large-surface liquid phase are passed in countercurrent to one another. This process step can be carried out particularly easily in washing columns equipped in particular with fillings or packings or comparable elements, such as bubble trays and the like. The cooled vapor condensate stream is introduced at the top of the column while the vapor sidestream to be condensed is introduced in countercurrent at the bottom of the column.

The condensation of the vapor sidestream may be carried out in a single stage and also in several stages.

If only a stable emulsion component of the condensate formed is used as the circulating stream in the manner described above, the process is generally not disrupted by unwanted deposits, more particularly of organic constituents, in the liquid circuit or rather in the washing column. If, nevertheless, problems should arise in special cases, a particular embodiment of the invention enables them to be solved as follows: by means of a stream of washing water containing no organic constituents or distinctly smaller quantities than the circulated aqueous primary stream, those parts of the apparatus threatened by the formation of coatings can be cleaned or washed continuously or periodically in order thus to eliminate possible disturbances. According to the invention, there is no need to introduce water from outside. Instead, part of the aqueous permeate stream from the following membrane separation stage can be circulated to act as the washing liquid.

In special cases, it can be useful slightly to modify the condensation of the vapor stream to be conditioned in the following manner: retaining the principle of condensation by direct heat exchange between the vapor stream and a circulated aqueous condensate stream, particularly readily condensable and separable components are separated from the vapor stream in a preceding partial condensation stage. The components in question may be, in particular, comparatively high-boiling organic components which can be condensed in advance and, if desired, separated off in this way. It is thus possible in such special cases to rule out or reduce secondary disturbances in the subsequent heat exchange by condensation through direct contact between the (residual) vapor stream and circulated liquid condensate. The vapor energy component removed in such a preliminary condensation stage will be kept as small as possible in consistency with the concept according to the invention of recycling energy as far as possible in the second energy exchange step described above. However, even in special cases such as these, it is possible by suitably guiding the second liquid stream to recover all the energy introduced via the vapor stream. To this end, the preliminary partial condensation is carried out by indirect energy exchange so that this part of the condensation energy is also available for reuse. In preferred embodiments of the process according to the invention, the partial preliminary condensation of the vapor stream to be purified is limited to such an extent that more than 50%, in particular more than 75% and better still more than 85% of all the condensation energy accumulating goes into the direct exchange between vapor and liquid vapor condensate.

The liquid stream leaving the first stage of the process (direct cooling) is delivered to the second energy transfer stage—designed as indirect cooling—in the form of an aqueous solution or emulsion of entrained organic constituents, optionally after removal of any continuous organic phase formed. The branching of the sidestream to be introduced into the membrane separation unit may take place before and/or preferably after this indirect cooling stage. The actual design of this indirect exchange of energy can be based on relevant expert knowledge.

After adjustment of the reduced temperature level optimized for the particular application, the liquid condensate stream is returned to the primary washing stage.

The sidestream branched off from this circulating stream, of which the volume is determined by the amount of condensate accumulating per unit of time in the primary process step, is subsequently subjected to separation in the membrane separation unit. The membranes available vary considerably in terms of chemical characteristics and separation efficiency, the choice of the particular membrane for each individual case being determined by the requirements of the separation process. More particularly, the following observations apply in this regard.

The conditioning of the aqueous organic phase can be carried out effectively and with high volume/time yields with the aid of modern technology. General specialist knowledge is documented, for example, in the books by JU.I. Dytnerskij "Membranprozesse zur Trennung flüssiger Gemische (Membrane Processes for Separating Liquid Mixtures)", VEB Deutscher Verlag für Grundstoffindustrie, Leipzig 1977, and by M. Cheryan "ULTRAFILTRATION HANDBOOK", Technomic Publishing Co., Inc., Lancaster, Basel, 1986. The choice and adaptation of the particular membrane separation process according to the nature and characteristics of the membranes selected and the special technology to be used is determined by the particular mixture to be separated. The impurity-laden aqueous phase can be conditioned in a single stage or even in several stages. The choice of suitable membranes extends from microfiltration via ultrafiltration and nanofiltration to reverse osmosis. Here, too, the technical procedure will be determined by the particular parameters of the mixture to be separated.

If the condensate is purified in several stages in the membrane separation stage, it can be particularly useful to provide semipermeable membranes increasing in steps in their separation efficiency in the successive separation stages. For example, microfiltration in the first stage can be combined with subsequent ultrafiltration or subsequent nanofiltration. However, the second separation stage may also be operated on the principle of reverse osmosis. Combinations of ultrafiltration and nanofiltration and of ultrafiltration and reverse osmosis are of course also possible. Finally, it is even possible to combine more than two separation stages with one another.

The choice and characteristics of the particular separation membranes used are determined by the particular circumstances prevailing. There are many types of semipermeable membranes of organic origin which may be used in the process according to the invention. However, it is generally preferred to use conventional ceramic membranes for the membrane separation stage of the process according to the invention. Commercially available inorganic membrane systems consist, for example, of a supporting material, for example based on carbon, in tube form with a membrane layer of metal oxides, for example zirconium dioxide, sintered thereon. The membranes are combined with one another to form tube modules. The modules are designed for high chemical and mechanical stability. Ceramic membranes of this type have important advantages. In particular, they are not only heat-resistant, they are also highly resistant to chemicals, for example to solvents and oxidizing agents. The membranes cannot be attacked by microorganisms. Inorganic membranes of the described type normally have high filtrate flow rates and, accordingly, perform with considerable efficiency, even at high viscosities. They enable elevated operating pressures, for example up to 10 bar, and high flow rates to be applied. The membranes have useful lives of up to several years and show only minimal signs of ageing. Differences in pressure and pressure surges have hardly any effect on the structure of the membranes. The literature on ceramic membranes is represented, for example, by the article by H. Hansmann entitled "Keramikmembranen in der Ultra- und Querstrom-Microfiltration (Ceramic Membranes in Ultra and Crossflow Microfiltration)", Behandlung und Aufbereitung von Industrieabwässern (Treatment and Conditioning of Industrial Wastewaters) in Jahrbuch für Umwelttechnik, Umwelt 92/93, MPV-Media-Partner-Verlagsagentur GmbH, Gütersloh and the information sheets on the product "Carbosep®" of TECH-SEP, Groupe Rhône-Poulenc, rue Penberton, Saint-Maurice-de-Beynost, Miribel, Cedex-FRANCE.

DETAILED DESCRIPTION OF THE DRAWINGS

Figure 1:
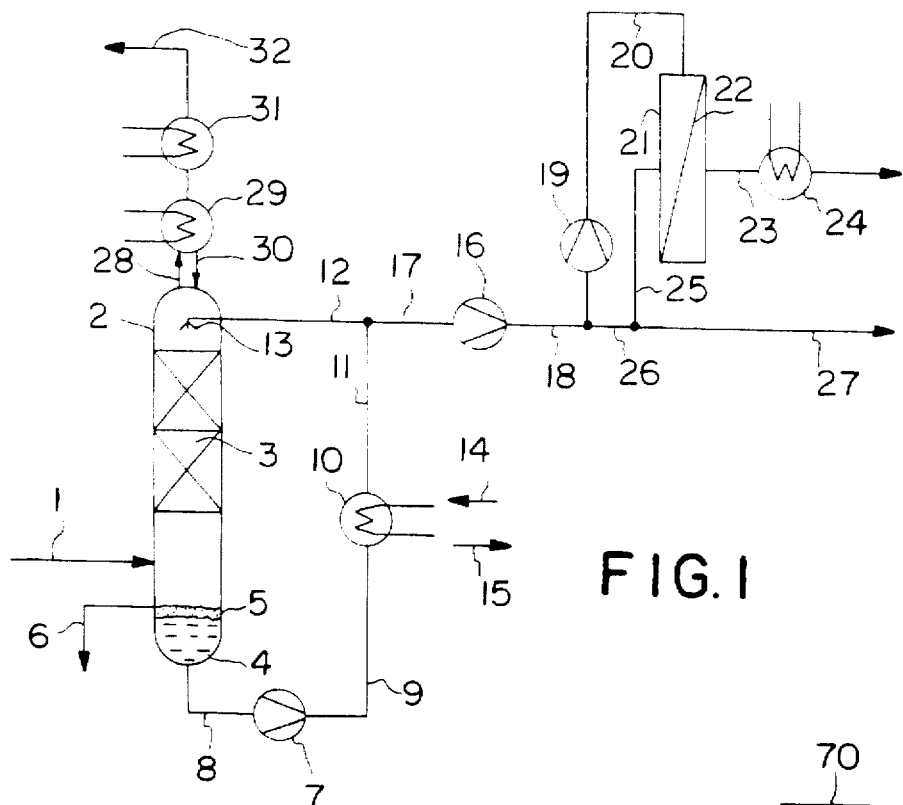
FIGS. 1 to 3 of the accompanying drawings illustrate embodiments of the working principle according to the invention.

The flow chart in FIG. 1 illustrates the principles of the process according to the invention as a single-stage process both in the condensation and energy transfer stage and in the following membrane separation stage.

The vapor stream to be purified (for example a vapor stream accumulating from drying with superheated steam and laden with steam-volatile organic components from the material to be dried) is delivered through pipe 1 to the lower part of the washing column 2, the exchange between vapor phase and large-surface liquid phase taking place in the washing column filled with a packing 3. The liquid vapor condensate flowing downwards through the washing column collects in the lower part of the washing column 2 where it separates into the stably emulsified aqueous liquid phase 4 and a floating oil/fatty phase 5. This part of the organic load to be separated from the vapor stream can be removed by simple phase separation through the pipe 6.

The stable aqueous emulsion 4 is removed through the pipe 8 at the bottom of the washing column by means of the pump 7 and is delivered through the pipe 9 to the indirect heat exchanger 10 for the recovery of heat. The aqueous emulsion cooled in a certain way is returned through pipes 11 and 12 to the head of the washing column 2 where it is applied, for example by spray nozzles 13, to the filling or packing 3. To take up the heat to be removed from the liquid condensate stream, the stream of the second and indirectly used cooling medium is delivered through 14 to the indirect heat exchanger 10 and removed therefrom through 15.

After the indirect heat exchange stage, a sidestream is removed from the circulating vapor condensate by the pump 16 through pipe 17 and delivered by the pump 19 through pipes 18 and 19 to the membrane separation unit 21 with the semipermeable membrane 22. The aqueous permeate stream can be removed from the membrane separation stage through 23 and, after a final heat exchange in 24 can be discharged for example into the wastewater. The retentate retained in the membrane stage is removed through pipe 25. It may be partly recirculated to the membrane separation stage by the pump 19 through the pipe 26 and partly (or even completely in the absence of such split recycling) removed through pipe 27 and, for example, reused.

Vapor streams of the type in question generally contain small quantities of non-condensable gases, more particularly a corresponding small inert gas component. This gas component is removed at the head of the washing column 2 through 28, subjected to post-condensation in the condenser 29 and separated into the liquid to be returned through pipe 30 and into the inert gas component which is removed through the pipe 32, optionally after passing through an additional heating stage 31. If this waste gas component still contains organic constituents, they may be reliably eliminated, for example, by delivering the gas stream removed through 32 to a combustion stage.

Figure 2:
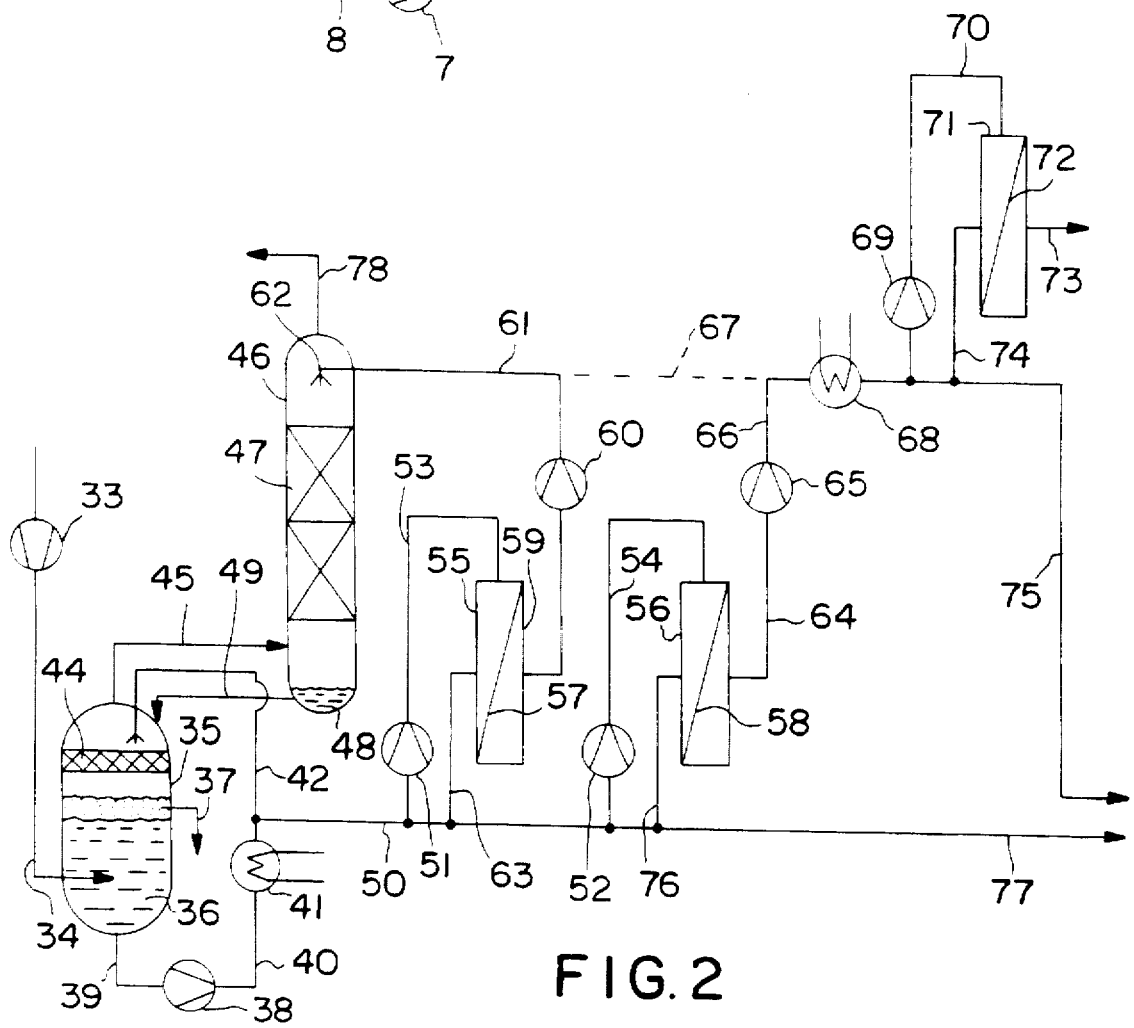

The process principle illustrated in FIG. 1 is illustrated in the form of a technologically refined embodiment in FIG. 2. The working principles according to the invention are embodied in this case, too; the only difference being that the vapor condensation stage and the following membrane separation stage now comprise several stages.

The vapor stream to be conditioned is delivered by the fan 33 through the pipe 34 to a holding tank 35 in which liquid vapor condensate 36 is present in a relatively large quantity. A separate at least predominantly organic phase collects on the surface of the hot aqueous organic emulsate phase and can be removed through 37. The hot vapor stream is directly introduced through pipe 34 into the hot aqueous emulsate phase 36 and at the same time, is condensed to a considerable extent. Liquid condensate is run off from the bottom of the holding tank 35 through 39 by means of the pump 38 and delivered through pipe 40 to the following indirect heat exchanger 41 which, basically, is comparable in design with the indirect heat exchanger 10 shown in FIG. 1. The circulated liquid vapor condensate stream leaves the indirect heat exchanger through pipe 42 in a predetermined manner and is then returned to the head of the holding tank 35 where it is sprayed onto a packing 44.

This first condensation stage is designed for substantial, but not complete condensation of the vapor stream introduced and/or for partial re-evaporation of already liquefied and circulated vapor condensate under the effect of the energy introduced through 34. The corresponding vapor components leave the head of the holding tank 35 through pipe 45 and are delivered to the lower part of a washing column 46 which is equipped with means 47 to enlarge the surface of the liquid phase and hence to improve heat exchange with the vapor phase introduced. The liquid phase 48 collects at the bottom of the washing column 46 and is returned through pipe 49 to the first holding tank 35.

After passing through the indirect heat exchanger 41, a sidestream is removed through pipe 50 from the circulating stream of liquefied condensate from the first condensation stage. This sidestream is at least partly delivered by the pump 51 through pipe 53 to the membrane separation unit 55 with the semipermeable membrane 57. Part of the liquid removed through 50 may—but need not—be delivered by the pump 52 through pipe 54 to a second membrane separation stage 56 with the semipermeable membrane 58. Accordingly, the two membrane separation stages 55 and 56 may be arranged in tandem or may even be at least partly operated in parallel. The tandem arrangement will be described first of all:

The condensate stream introduced through pipe 53 into the membrane separation stage 55 is divided into a permeate stream and a retentate stream. The permeate leaves the membrane separation stage through pipe 59 by means of the pump 60 and is returned through pipe 61 to the head of the washing column 46 where it is sprayed, for example by means of spray nozzles 62, onto the packing or filling elements 47. The retentate of the separation stage 55 is removed through pipe 63. It may be partly returned by the pump 51 through pipe 53 to the same membrane separation stage, although at least part of this retentate stream is introduced through pipe 54 into the following membrane stage 56 by the pump 52. After passing through the semipermeable membrane 58, the permeate leaves the separation stage 56 through 64 under the effect of the pump 65. The retentate from this second separation stage is removed through 76. It may be partly returned through pipe 54 to the same separation stage by the pump 52, but is at least partly removed through 77, for example to enable the organic components isolated here to be reused.

The parallel operation of the two separation stages only differs from the tandem arrangement insofar as the cooled vapor stream removed through pipe 50 is delivered to the two separation stages 55 and 56 by the pumps 51 and 52 and processed therein.

FIG. 2 illustrates another method of conditioning the permeate stream 64 or 66 removed from the separation stage 56. In this case, the temperature envisaged for the following, third membrane separation stage is adjusted in the water-based liquid stream to be conditioned via the heat exchanger 68. The liquid stream is introduced into the membrane separation stage 71 with the semipermeable membrane 72 by the pump 69. The permeate passing through the membrane is removed through 73 and, for example, may be discharged into the wastewater. The retentate of the separation stage 71 is removed through pipe 74. It may again be partly returned to this membrane separation stage through pipe 70 by means of the pump 69 and at least partly and, preferably, predominantly discharged through the pipe 75. Once again, the enriched organic components may be reused.

Any non-condensable gaseous components present in the vapor stream 34 introduced are removed from the head of the washing column 46 through the pipe 78, optionally with the aid of the individual measures illustrated in FIG. 1 in connection with the corresponding disposal of a non-condensable gas component.

Figure 3:
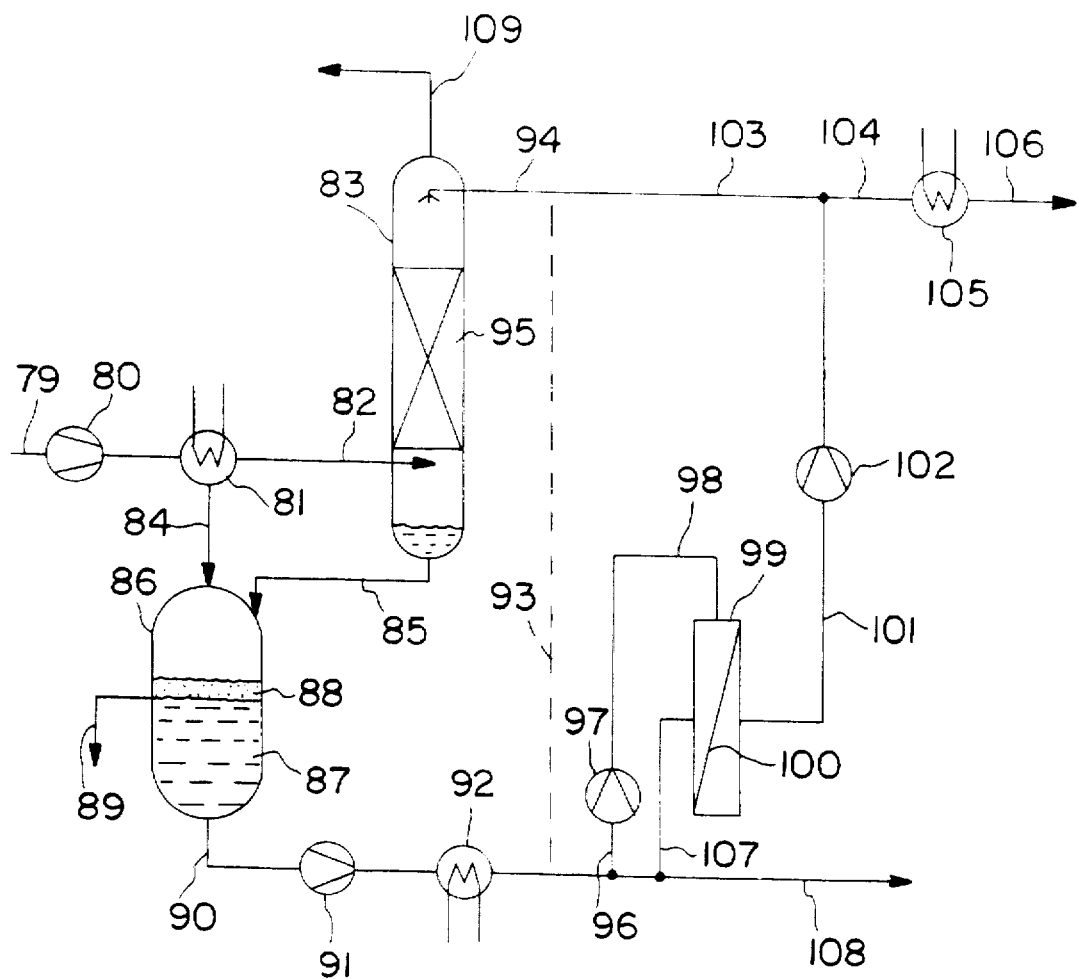

Finally, FIG. 3 illustrates the above-mentioned modification of the process according to the invention in which particularly readily condensing components are separated beforehand from the vapor stream in rtial preliminary condensation and are thus removed from the subsequent multistage treatment of the vapor stream. More specifically, the vapor stream delivered through pipe 79 by the fan 80 is introduced into an indirect heat exchanger 81 in which the particularly rapidly condensing components are converted into liquid phase and are removed from the heat exchanger through 84. The remaining vapor component of the vapor stream is delivered through pipe 82 to the lower part of the washing column 83 which it enters in countercurrent to the liquid phase which is delivered to the head of the washing column through 94 and sprayed onto the packing or filling elements 95.

The liquid phase collecting at the bottom of the washing column 83 is removed through pipe 85 and, in the same way as the first condensate from the partial condensation through pipe 84—is introduced into the holding tank 86. The stable liquid emulsion phase 87 collects in this holding tank and is covered by the separating, at least predominantly organic constituents 88 which are removed through 89. The emulsion condensate is removed at the bottom of the holding tank through 90 by the pump 91 and delivered to the indirect heat exchanger 92. This heat exchanger is constructed in the same way as the heat exchanger 10 in FIG. 1. The cooled vapor condensate stream may be partly returned to the head of the washing column 83 through pipes 93 and 94. The cooled vapor condensate stream is at least partly delivered to the membrane separation Sage 99 by the pump 97 through pipes 96 and 98. If desired, the process may also be modified by delivering the cooled vapor condensate stream as a whole—after it has passed through the indirect heat exchanger 92—to the membrane separation unit 99 by means of the pump 97.

The permeate passing through the semipermeable membrane 100 is removed through pipe 101 by the pump 102. The aqueous permeate may be partly delivered to the head of the washing column 83 through pipes 103 and 94, but is at least partly removed from the circuit through the pipes 104 and 106 after readjustment of the condensate temperature in the heat exchanger 105.

The retentate of the membrane separation unit 99 is removed through pipe 107. It may be partly returned to the separation unit through the pipes 96 and 98, but is at least partly removed from the circuit through the pipe 108. The organic constituents of the vapor stream to be purified may be reused as required. Any non-condensable gaseous components accumulating collect at the head of the washing column 83 where they are removed through pipe 109. They may be processed in the same way as described more specifically for the inert gas component of FIG. 1.

EXAMPLES

Example 1

An aqueous slurry of a commercial detergent (Persil®, Henkel KGaA) was dried with superheated steam in a NIRO "Minor" experimental spray-drying tower. To this end, superheated steam is introduced into the spray drying tower at a temperature of around 280° C. The steam exit temperature is 140° C. The steam is circulated and, before re-entering the tower, is heated to the necessary drying temperature of 280° C. in an electrical heat exchanger. The fine component of the dried powder is removed in a cyclone and a filter.

Under the working conditions described above, the aqueous slurry is spray dried in such quantities that the vapor stream to be separated off and conditioned accumulates in a quantity of 7.6 kg/h.

The condensation and conditioning of the vapor stream—on the one hand with recovery of energy and on the other hand with separation of the emulsion condensate initially accumulating—is carried out in accordance with the teaching of the invention. To this end, liquefied and partly cooled vapor condensate is circulated through a washing column in which liquefied vapor condensate is removed at the bottom of the washing column and, after separation of the floating fatty phase, is passed through an indirect heat exchanger and reintroduced as a partly cooled liquid phase at the top of the washing column. The vapor stream to be condensed is introduced at the lower end of the washing column in countercurrent to the liquid vapor condensate flowing downwards through the washing column. The following material and process parameters apply to this circulation system:

Quantity of vapor stream introduced: 7.6 kg/h
Temperature of the liquefied vapor condensate removed at the bottom of the washing column and subsequently transferred to the indirect heat exchange stage: 97° to 100° C.
Temperature of the circulating vapor condensate stream after leaving the indirect heat exchange stage: 85° C.
Circulation rate of the liquid vapor condensate stream: 283.5 l/h A floating liquid phase of organic components, of which the principal components are $C_{12-20}$ fatty alcohols, forms on the surface of the liquid vapor condensate collecting at the bottom of the washing column in a quantity of around 0.5% by weight, based on the total condensate (water content approx. 14% by weight). The principal components of this floating organic liquid phase are determined as follows:

$C_{12}$ fatty alcohol: 0.6% by weight
$C_{14}$ fatty alcohol: 2.0% by weight
$C_{16}$ fatty alcohol: 24.9% by weight
$C_{18}$ fatty alcohol: 41.4% by weight
$C_{20}$ fatty alcohol: 1.1% by weight The lower aqueous phase of the overall condensate (approx. 99.5% by weight) contains the organic constituents and, in particular, the fatty alcohols present here, too, in the form of a stable emulsion. The following figures apply to the composition of this aqueous lower phase:

$C_{14}$ fatty alcohol: 0.001% by weight
$C_{16}$ fatty alcohol: 0.006% by weight
$C_{18}$ fatty alcohol: 0.009% by weight The lower emulsate phase is present as a milky emulsion. It is subsequently concentrated by microfiltration, the fatty alcohols being recovered in concentrated form. The permeate accumulating in this microfiltration stage is a completely clear aqueous liquid phase. The microfiltration process is carried out as follows:

A monolithic inorganic membrane of the "Kerasep TM" type manufactured by Tech-Sep is used. The support consists of $Al_2O_3/TiO_2$ and has a diameter of 22 mm. It contains 19 membrane channels (multi-channel module). The diameter of each membrane channel is 2.5 mm. Accordingly, for a module length of 856 mm, the membrane surface measures 0.12 m². A membrane with a 0.2 μm cutoff was used for filtration.

The following operating parameters were adjusted for microfiltration:
Transmembranal pressure: 1 bar
Temperature: approx. 80° C.
Crossflow rate: 5.6 m/s
Av. filtrate flow: 500–600 l/hm²

The condensate is concentrated in a ratio of 1:40 by partial recycling. The COD values of the permeate stream are in the range from 200 to 300 mg/l and are largely independent of the concentrating organic load of the emulsion phase delivered to the microfiltration stage.

Example 2

A detergent formulation of which the anionic surfactants consistent of fatty alcohol sulfates (predominantly with a chain length of $C_{16}$–$C_{18}$) was dried with superheated steam in an experimental spray drying tower. The average evaporation rate was 8 kg/h. The excess vapors were removed from the circuit at a temperature of 120° C. and totally condensed in the condensation column shown in FIG. 1. The spray drying tower was operated as follows:

Vapor quantity (1): 12 kg/h (including 4 kg/h propellent steam for two-component nozzle)
Condensate circulation rate (9): 290 l/h
Condensation temperature before HE (9): 97° C.
Condensation temperature after HE (11): 75° C.
Org. upper phase deposited in (6): approx. 12 g/h (water content: 14%)
Cooling water entry temperature (14): 70° C.
Cooling water exit temperature (15): 90° C.
Cooling water volume: 320 l/h
Heat dissipated: 20.880 kJ/h=7.47 kW The excess vapor (1) and lower condensate phase (8) had the following loads:

| Parameter | Vapor (1) | Condensate (8) |
| --- | --- | --- |
| Chemical oxygen demand, COD (mg/l) | 4330 | 830 |
| Organic load as measured by gas chromatography (mg/l) | 1000 | 200 |
| $C_{12-20}$ fatty alcohols (mg/l) | 640 | 90 |

The condensate (17) removed from the circuit was further purified in a microfiltration stage (21). To prevent blockage of the membrane by high-boiling fatty alcohols, the microfiltration stage was operated at a condensate temperature of 85° C.

The following parameters were adjusted and measured:
Transmembranal pressure: 4 bar
Circulation stream (20): 1500 l/h
Permeate stream (23): 78 l/h
Retentate stream (27): 3.9 l/h
Membrane area: 0.12 m²
Membrane type: Kerasep (cutoff limit 0.2μ)

The organic load of the permeate stream (23), measured as the chemical oxygen demand (COD), was 215 mg/l. Based on the vapor stream at the column entrance, this represents a reduction of 95%. The load of the retentate (27), measured as COD, was 16.600 mg/l (initial value of the condensate: 830 g/l).

Example 3

A detergent formulation in which alkyl benzene sulfonates were used as the anionic surfactants was dried with superheated steam. The excess vapors were again condensed in the condensation column shown in FIG. 1. The operating conditions corresponded to Example 2, except that the upper phase deposited at the bottom (6) of the column was only removed at the end of the test because of the very small quantity.

The following condensate loads were measured:

| Parameter | Vapor (1) | Condensate (8) |
| --- | --- | --- |
| Chemical oxygen demand, (mg/l) | 1640 | 850 |
| Alkylbenzene (mg/l) | 38 | 10 |

The condensate stream (8) was purified in the membrane unit at around 80° C. In this case, the following parameters were adjusted and measured:
Transmembranal pressure: 1.3 bar
Circulating stream (20): 2000 l/h
Permeate stream (23): 21 l/h
Retentate stream (27): 2 l/h
Membrane area: 0.12 m²
Membrane type: Kerasep (cutoff limit 0.1μ)

The organic load of the permeate stream (23), measured as the chemical oxygen demand (COD), was less than 150 mg/l while the alkyl benzene concentration was less than 1 mg/l. This represents a reduction in COD, based on the vapor stream (1), of more than 90%.

We claim:

1. The process of conditioning a vapor stream of superheated steam laden with steam-volatile organic components, comprising condensing said vapor stream to form a condensate containing water and said organic components and simultaneously recovering the heat of condensation of said vapor stream by direct contact with a circulated, cooled liquid stream of condensed vapor stream, transferring the energy taken up by the circulated, cooled liquid stream of condensed vapor stream to a second carrier by indirect heat transfer, removing a sidestream from the condensate containing water and said organic components, and subjecting said sidestream to separation by a membrane.

2. A process as in claim 1 wherein said sidestream is maintained at a temperature which prevents blockage of said liquid stream and the surface of said membrane by condensing organic components.

3. A process as in claim 1 including removing a portion of said organic components from said condensate by phase separation prior to subjecting said sidestream to separation by a membrane.

4. A process as in claim 1 carried out at ambient pressure and wherein said circulated liquid stream has a maximum temperature of about 90° C. to about 100° C.

5. A process as in claim 4 wherein said circulated liquid stream has a minimum temperature of about 60° C. to about 70° C.

6. A process as in claim 1 wherein said condensing step is carried out by introducing said vapor stream to the bottom portion of a countercurrent washing apparatus provided with fillings or packings, and introducing the condensate to the upper portion of said washing apparatus.

7. A process as in claim 6 wherein said condensing step is carried out in multiple steps.

8. A process as in claim 1 wherein said step of subjecting said sidestream to separation by a membrane is carried out in multiple steps.

9. A process as in claim 1 wherein said membrane is made of inorganic materials.

10. A process as in claim 1 wherein said vapor stream is obtained from a drying process of materials used in the production of wetting agents, detergents or cleaning compositions and wherein said drying process employs superheated steam as the drying gas.

11. A process as in claim 1 for the recovery of flavorings or fragrances.

12. A process as in claim 1 for the conditioning of superheated steam from a distillation-based separation process for multicomponent mixtures of at least partly organic origin.

* * * * *